US010857035B2

United States Patent
Padovani

(10) Patent No.: US 10,857,035 B2
(45) Date of Patent: Dec. 8, 2020

(54) REMOVABLE SPOILER FOR SKI GOGGLES

(71) Applicant: Carl Zeiss Vision Italia S.p.A., Castiglione Olona-Varese (IT)

(72) Inventor: Roberto Padovani, Malnate (IT)

(73) Assignee: Carl Zeiss Vision Italia S.p.A, Castiglione Olona-Varese (IT)

( * ) Notice: Subject to any disclaimer, the term of this patent is extended or adjusted under 35 U.S.C. 154(b) by 0 days.

(21) Appl. No.: 14/673,296

(22) Filed: Mar. 30, 2015

(65) Prior Publication Data

US 2015/0272784 A1    Oct. 1, 2015

(30) Foreign Application Priority Data

Mar. 28, 2014  (AT) .......................... GM50046/2014
Mar. 28, 2014  (DE) .................... 20 2014 002 709 U

(51) Int. Cl.
*A61F 9/02*    (2006.01)

(52) U.S. Cl.
CPC ........ *A61F 9/029* (2013.01); *A61F 2009/021* (2013.01)

(58) Field of Classification Search
CPC .......... A61F 9/025; A61F 9/028; A61F 9/029; A61F 9/02
See application file for complete search history.

(56) References Cited

U.S. PATENT DOCUMENTS

| | | | | |
|---|---|---|---|---|
| 2,026,741 A | * | 1/1936 | Kintz ...................... | A61F 9/025 2/10 |
| 2,393,837 A | * | 1/1946 | Swanson .................. | G02C 5/02 2/13 |
| 2,496,969 A | * | 2/1950 | Wentworth .............. | G02C 5/00 351/130 |
| 3,120,002 A | * | 2/1964 | Blumenthal .............. | A61F 9/02 2/9 |
| 3,133,982 A | * | 5/1964 | Janz ........................ | A61F 9/026 2/426 |
| 3,383,707 A | * | 5/1968 | McNeill ................... | G02C 9/02 2/12 |
| 3,517,393 A | * | 6/1970 | Beauchef ............... | G02C 11/08 2/436 |

(Continued)

FOREIGN PATENT DOCUMENTS

DE    30 46 046 A1    7/1982
DE    87 09 530 U1    12/1987

(Continued)

OTHER PUBLICATIONS

English translation and the search report of the Austrian Patent Office dated Feb. 4, 2015 in Austrian patent application GM50046/2014-1,2 on which the claim of priority is based.

(Continued)

*Primary Examiner* — Sally Haden
(74) *Attorney, Agent, or Firm* — Walter Ottesen, P.A.

(57) ABSTRACT

The invention is directed to ski goggles having a frame with a frame back side directed toward the wearer's face during use. A frame front lies opposite the frame back side and a frame edge is directed laterally outward with an upper frame-edge portion. A goggle lens is supported by the frame and a retaining strap, during normal use, holds the ski goggles on the wearer's head. A spoiler can be releasably connected to the upper frame-edge portion.

21 Claims, 5 Drawing Sheets

(56) References Cited

U.S. PATENT DOCUMENTS

| | | | | |
|---|---|---|---|---|
| 3,675,991 | A | * | 7/1972 | Brenn .................. A45D 44/22 351/158 |
| 3,782,810 | A | * | 1/1974 | Marker .................. A61F 9/025 2/432 |
| 4,240,718 | A | * | 12/1980 | Wichers ................ G02C 3/003 351/111 |
| 4,264,988 | A | | 5/1981 | Specht |
| 4,556,995 | A | | 12/1985 | Yamamoto |
| 4,630,321 | A | * | 12/1986 | Sagemuehl ............ A61F 9/029 2/426 |
| 4,977,627 | A | | 12/1990 | Metcalfe et al. |
| D321,703 | S | * | 11/1991 | Grau ....................... A61F 9/02 D16/313 |
| 5,138,723 | A | * | 8/1992 | Bolle ....................... A61F 9/02 2/430 |
| 5,576,775 | A | * | 11/1996 | Bolle ....................... A61F 9/02 2/436 |
| 5,657,106 | A | * | 8/1997 | Herald, Jr. ............... G02C 3/02 2/437 |
| 6,105,177 | A | * | 8/2000 | Paulson .................. A61F 9/027 2/431 |
| 6,227,664 | B1 | * | 5/2001 | Pavlak .................... A61F 9/026 2/437 |
| D462,979 | S | * | 9/2002 | Fairclough .............. G02C 9/02 D16/304 |
| 6,959,988 | B1 | * | 11/2005 | Sheldon .................. G02C 1/04 351/103 |
| 8,820,920 | B2 | * | 9/2014 | Chang .................... G02C 5/006 351/92 |
| 9,846,316 | B2 | * | 12/2017 | Tipp ....................... G02C 11/08 |
| 2002/0029408 | A1 | * | 3/2002 | Lindahl .................. A61F 9/025 2/426 |
| 2003/0033661 | A1 | * | 2/2003 | Huh ....................... A61F 9/028 2/436 |
| 2004/0111779 | A1 | * | 6/2004 | Gagnon .................. A42B 3/20 2/9 |
| 2007/0261155 | A1 | * | 11/2007 | Tabacchi ................ A61F 9/025 2/439 |
| 2009/0151057 | A1 | * | 6/2009 | Lebel ..................... A61F 9/029 2/452 |
| 2014/0157496 | A1 | * | 6/2014 | Ginther .................. A61F 9/025 2/439 |

FOREIGN PATENT DOCUMENTS

| | | |
|---|---|---|
| DE | 20 2004 001 735 U1 | 6/2004 |
| DE | 10 2004 005 757 A1 | 8/2005 |
| DE | 10 2004 063 921 A1 | 5/2006 |
| EP | 2 060 246 A1 | 5/2009 |
| SI | 9700061 A | 10/1998 |

OTHER PUBLICATIONS

English translation and the search report of the German Patent Office dated Jan. 19, 2015 in German patent application 20 2014 002 709.9 on which the claim of priority is based.

Zsolt, W., ""iON" ski goggles with camera for dramatic experiences on the slopes", derStandard.at >Web>Innovationen, http://derstandard.at/1326503711981/Wintersport-Kamera-Skibrille-iON-fuer-dramatic . . . ,Vienna, Jan. 25, 2012, one page and English translation.

* cited by examiner

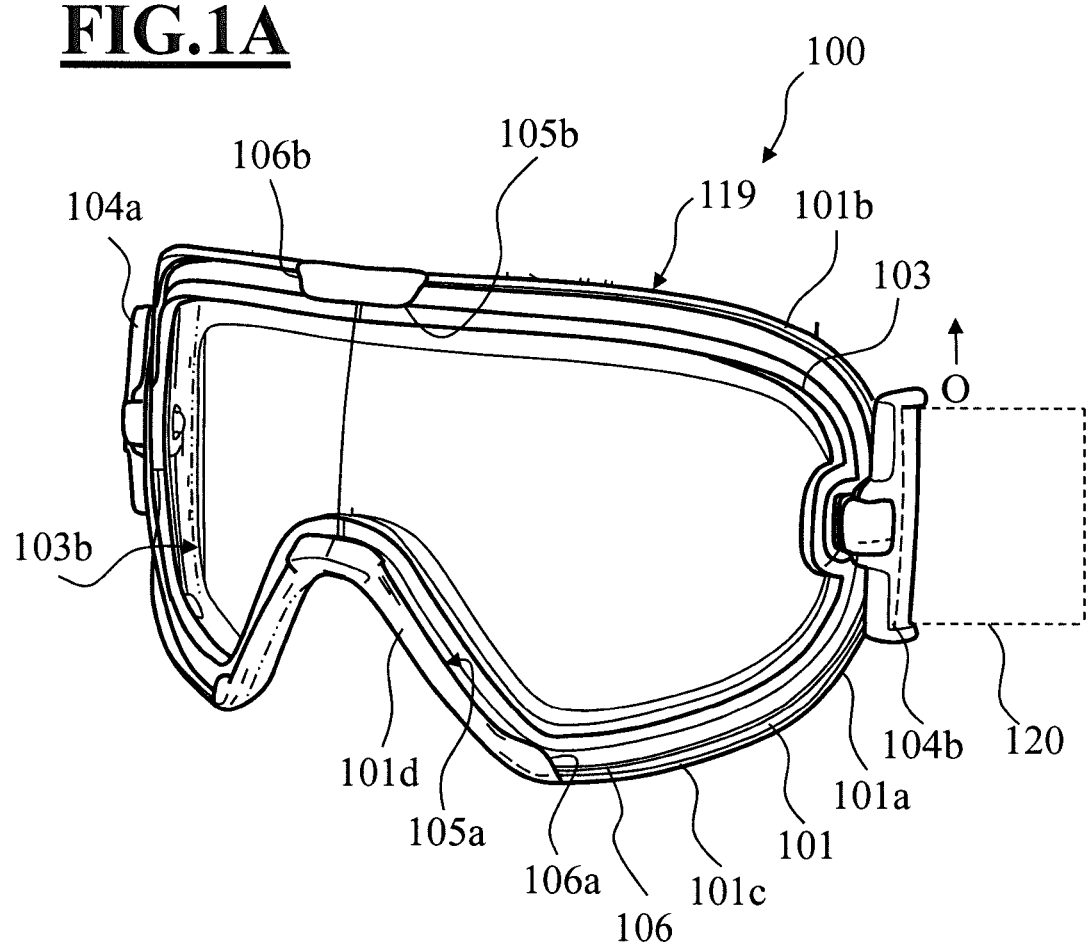

REMOVABLE SPOILER FOR SKI GOGGLES

CROSS REFERENCE TO RELATED APPLICATIONS

This application claims priority of German patent application no. 20 2014 002 709.9, filed Mar. 28, 2014, and Austrian patent application no. GM50046/2014, filed Mar. 28, 2014, and the entire contents of both are incorporated herein by reference.

BACKGROUND OF THE INVENTION

Ski goggles are known in many forms. The present invention is based on ski goggles with a frame, with a goggle lens which is supported by the frame and has a surface (front surface) directed toward the wearer's face during normal use and a surface (rear surface) directed away from the wearer's face during normal use, with a frame pad which is connected to the frame and can be brought to rest on the wearer's face, and with a retaining strap for holding the ski goggles on the wearer's head. Ski goggles of this type are described, for example, in DE 87 09 530 U1; U.S. Pat. No. 4,556,995; DE 10 2004 005 757 A1; or, EP 2 060 246 A1.

Within the context of the present invention, frame is understood as meaning those parts which serve as a support for the goggle lens. The frame is generally made from a plastic preferably having a certain degree of elasticity. The frame generally completely surrounds the outer edge of the goggle lens.

The frame is generally curved concavely in a manner adapted to the curvature of the wearer's face.

Within the context of the present invention, a goggle lens is understood as the transparent body through which the wearer looks during normal use and which determines the field of view of the wearer. The goggle lens can be made of a plastic. The goggle lens can also be flexible. The goggle lens can optionally also have a (possibly prescribed) dioptric effect. However, it may also be formed as a lens without dioptric effect. It is generally made in one piece and is provided for both eyes to look through.

The frame pad is mostly made of a foam material having greater elasticity than the frame, in order to be able to adapt to the contour of the wearer's face.

Therefore, the frame and the frame pad are generally not made in one piece or of the same material. In most cases, there is an adhesive connection between frame and frame pad.

The retaining strap is generally composed of a length-adjustable textile or rubber strap. The retaining strap is mostly fastened to the frame. However, it can also be fastened to the goggle lens.

EP 2 060 246 A1 describes ski goggles with a surround in the form of a frame, with a lens arranged on the latter and designed as a viewing lens, with a face rest as a frame pad, and with a retaining strap. Arranged above the lens, a visor protrudes above the front face of the lens and has air inlet openings. In the central area, the visor is at least 5 mm, in particular at least 10 mm above the viewing lens of the ski goggles. It forms an air guide device, by which the air flowing onto the ski goggles is guided and/or diverted in a targeted manner. The visor is arranged at a distance from the frame in such a way that air can flow in through the air inlet openings above the visor. The air inlet openings are formed at a distance from the front edge of the visor by arches. The arches have a free height of at least 2 mm, in particular at least 5 mm. They have a lateral extent of at least 10 mm, in particular at least 20 mm. Here, the lateral extent is preferably at least three times, in particular at least five times as great as the free height of the arches, which among other things gives them a particularly advantageous design. The air inlet openings are oriented in such a way that, when the ski goggles are being used, air approaching from the front can flow through them efficiently, that is, largely without loss of speed.

The visor is shaped and arranged in such a way that, seen from the side, it slopes gently downward relative to the lens in the central area. The visor can for example be plugged onto the frame. For this purpose, it has a central plug device and lateral plug devices. The plug devices can be latched into seats matching them in the head strap sidepiece. If need be, the visor can therefore be easily detached. When plugged on, the visor is spaced apart from the frame in such a way that an air inlet gap is formed between them.

In the central area of the visor, air can flow in above and below the visor. The air thus flows through the air inlet opening and the air inlet gap. The approaching air is deflected downward through ca. 90° by the visor, such that it flows along the back of the lens and thus prevents misting thereof.

The flow of air entering the lateral areas above and below the visor can diverge from the central area of the visor and emerge upward through the slit in front of the face rest.

FIG. 1 and FIG. 2 of the document show that the face rest protrudes slightly above the frame. In the illustrative embodiment shown, the vertical extent of the face rest appears not to reach beyond the free height of the arches.

U.S. Pat. No. 4,556,995 describes ski goggles with a protective lens, a frame surrounding the protective lens and configured in one piece with upper, lateral and lower frame portions, and two retaining straps lying opposite each other and used to secure the ski goggles on the user's head. At least along the upper frame portion, the frame is provided with a releasably fastenable collision protector. The collision protector extends perpendicular to the front face of the protective lens. However, it has no extent protruding above the frame in the lateral direction.

Although the above-described ski goggles have proven useful in principle, the wearing comfort experienced by the user generally depends on whether a helmet is being worn and, if so, which helmet. A helmet and ski goggles are not generally designed matching each other, such that neither the ski goggles nor the helmet protects the skier's forehead from cold air, which is very unpleasant, particularly at very low temperatures.

DE 20 2004 001 735 U1, DE 10 2004 005 757 A1 and DE 10 2004 063 921 A1 describe an air guide device in the form of a free-form part, of which the reverse contour corresponds to the outer contour of a helmet in the forehead area or can be adapted thereto. In the illustrative embodiments described in these documents, the ski goggles are of a design matching the free-form part, such that the above-described problem presumably does not arise.

SUMMARY OF THE INVENTION

An object of the invention is therefore to provide ski goggles which protect the skier's forehead from cold air when wearing a helmet whose viewing opening is not designed complementing the outer contour of the ski goggles. Correspondingly, an object of the invention is also to provide a protective device for protecting the skier's forehead from cold air.

The ski goggles according to the invention have a frame, a goggle lens which is supported by the frame and which, during normal use, has a surface directed toward the wearer's face, and a surface directed away from the wearer's face, and a retaining strap for holding the ski goggles on the wearer's head. The ski goggles according to the invention can have a frame pad which is connected to the frame and which is brought to rest on the wearer's face during normal use. The frame has a frame reverse directed toward the wearer's face during normal use, a frame front lying opposite the frame reverse, and a frame edge directed laterally outward. The frame edge has an upper frame-edge portion, which is oriented upward during normal use of the ski goggles, that is, when the wearer is wearing the ski goggles (generally via the helmet) by means of the retaining strap, and when the wearer's head is upright. According to the invention, the ski goggles have a spoiler, which can be connected releasably to this upper frame-edge portion.

This spoiler ensures that the gap between helmet and goggles is bridged and ensures that the skier's forehead is protected from cold air.

Correspondingly, the spoiler according to the invention comprises a fastening mechanism for releasable connection to an upper frame-edge portion of the ski goggles. For this purpose, the spoiler can, for example, have one or more latches, which are arranged on an underside of the spoiler and can engage and lock releasably in one or more corresponding latch openings in the upper frame-edge portion. In addition, guide webs or guide pins can also be provided on the underside of the spoiler and can be introduced into corresponding guide openings in the upper frame-edge portion in order to align spoiler and frame relative to each other preferably with a form fit, but they do not themselves have a latching or locking function.

The object of the invention is achieved in full by the above-described embodiments of ski goggles and spoiler.

During normal use of the ski goggles, that is, when the wearer is wearing the ski goggles and the helmet and when the wearer's head is upright, the spoiler protrudes preferably above the frame and in this way fills the gap between the top edge of the ski goggles and the bottom edge of the face opening of the helmet. This prevents cold air from flowing onto the otherwise exposed part of the skier's forehead, particularly during skiing.

The particular suitability of the ski goggles according to the invention for the majority of commercially available ski helmets is ensured if the spoiler protrudes above the frame by 0.4 cm to 2 cm in a central area, that is, at the center of the face in the continuation of the nose. If the distance above is chosen in the range of between 0.4 and 1.5 cm or between 0.4 cm and 1 cm, the skier will generally find an optimally fitting spoiler.

Since the bottom edge of the face opening of the majority of the helmets curves in an arc shape, it has proven useful for the spoiler to also have a complementary configuration. Accordingly, the spoiler according to the invention is preferably designed curving laterally upward in an arc shape. Even when the contours of ski goggles and helmet do not complement each other in an optimal manner, the free gap accessible to the air between helmet and ski goggles in the forehead area of the skier is sufficiently small.

If the spoiler curves laterally upward in an arc shape, it is advantageous if the radius of curvature is chosen between 10 cm and 100 cm. A curvature with a radius in this range ensures a substantially complementary adaptation to the shape of the helmet. Radii of curvature of between 15 cm and 90 cm or between 20 cm and 80 cm or even between 30 cm and 70 cm are particularly suitable.

In a particularly advantageous embodiment of the spoiler, the latter has a spoiler portion which is directed laterally upward away from the upper frame-edge portion and which is designed in such a way that, when the ski goggles are being used as intended by the skier, air that impacts the spoiler from the front is deflected upward and/or sideways with respect to the wearer's face. This prevents the air stream from directly impacting the skin of the face. In this case too, air contact is no longer felt to be so unpleasant by the skier.

The spoiler according to the invention can also have at least one air inlet or air inlet recess which, during normal use of the ski goggles, ensures that air impacting the spoiler from the front is deflected into the space formed, during normal use of the ski goggles, between the goggle lens and the eye region of the wearer's face. Misting of the ski goggles is effectively prevented by this measure.

Two variants of these ski goggles are that at least one of the air inlet recesses is designed as an opening in the spoiler, or that at least one of the air inlet recesses is designed as an opening between spoiler and frame. In the first variant, the openings are thus introduced directly into the spoiler, while in the second variant the openings are formed only by the fact that spoiler and frame are brought to rest on each other but do not bear with a contact fit on each other over the entire contact surface. Of course, it is also possible for the ski goggles to have openings of the first-mentioned type and openings of the second variant.

In principle, the air inlet openings/recesses can be arranged at any locations on the spoiler. However, it is expedient if the spoiler has a laterally downwardly pointing spoiler portion which is directed toward the upper frame-edge portion and which has at least one of the air inlet recesses. On the one hand, this ensures efficient ventilation, and, on the other hand, air removal is improved if no or fewer openings are provided on the upper part of the spoiler.

The frame too can have openings provided for ventilation. These openings are arranged, in the perpendicular direction to the surface directed toward the wearer's face during normal use, between the goggle lens and the frame pad. These ventilation openings permit a direct supply of air to the reverse of the goggle lens without further filtering, and this effectively prevents misting. The diameter of the preferably cylindrical openings is only between ⅟₂₀ and ⅕ of the thickness of the frame. Their number is preferably between 20 and 200.

The ventilation openings can extend parallel to the surface of the goggle lens directed toward the wearer's face during normal use. It is also possible for them to extend in the vertical direction during normal use. When suitably arranged, they can allow air to flow from below into the hollow space between the goggle lens and the face and allow air to flow upward out of the hollow space.

It is also expedient if the spoiler has a seat for electronic parts. Such electronic parts can be, for example, one or more cameras, a locating device based for example on the Global Positioning System (GPS), a mobile telephone device or the like.

The spoiler can, for example, be made at least in part from a flexible plastic having a modulus of elasticity of between 2 N/mm$^2$ and 100 N/mm$^2$. A risk of injury is then reduced in the event of a fall. At the same time, however, dimensional stability is also ensured.

It has proven advantageous if the spoiler is made at least in part from the same material as the frame. On the one hand, this ensures the compatibility with the frame, and, on the other hand, the manufacturing costs can thereby be kept to an economically reasonable level.

The frame is preferably made in one piece or two pieces so as to be able to be manufactured cost-effectively.

The frame can be made at least in part from a flexible plastic having a modulus of elasticity of between 1 N/mm$^2$ and 500 N/mm$^2$. Ski goggles with such an elasticity have proven extremely comfortable to wear.

It is not only the frame that is critical as regards wearing comfort, but also, and to a particular extent, the elasticity of the frame pad. Tests have shown that it is expedient if the frame pad is made at least in part from an elastic foam having a modulus of elasticity of between 0.02 N/mm$^2$ and 2 N/mm$^2$.

BRIEF DESCRIPTION OF THE DRAWINGS

The invention will now be described with reference to the drawings wherein:

FIG. 1A shows the ski goggles of FIG. 1 with a strap and without the spoiler;

DESCRIPTION OF THE PREFERRED
EMBODIMENTS OF THE INVENTION

Figure 1:
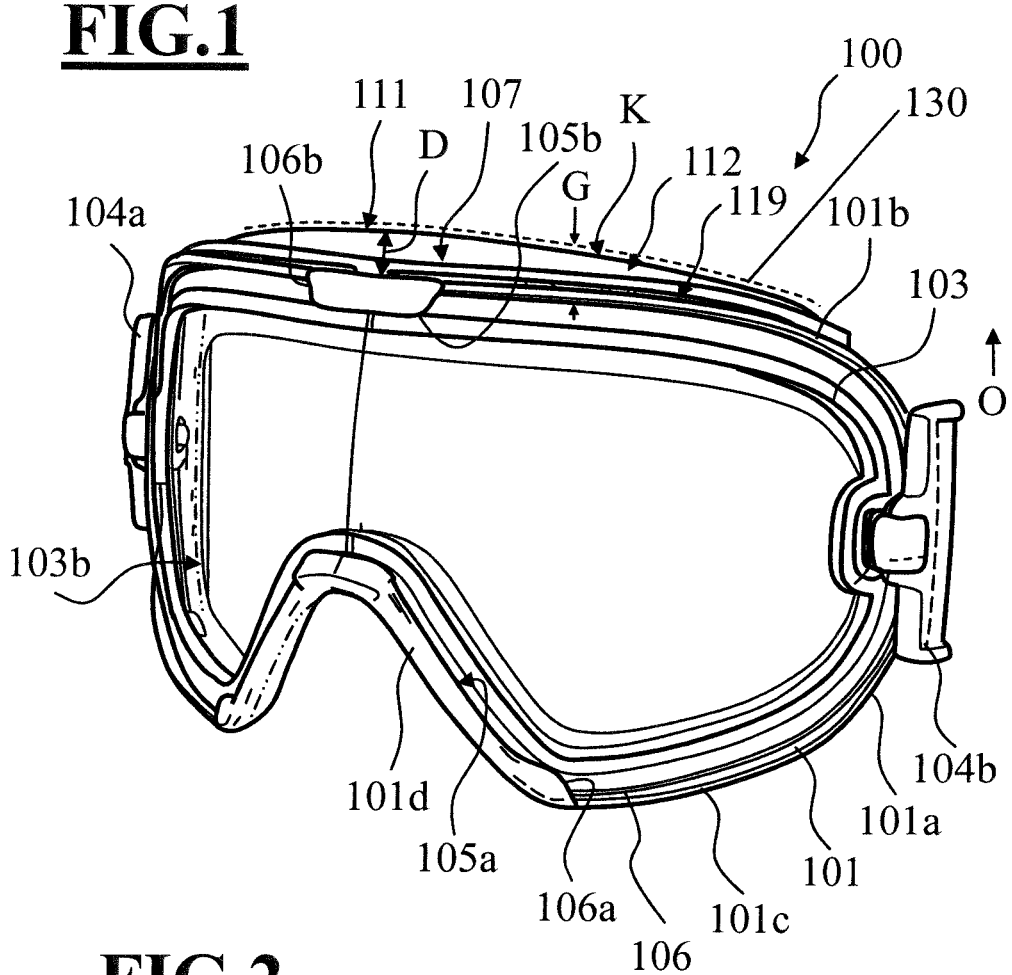
FIG. 1 shows an illustrative embodiment of ski goggles according to the invention in a three-dimensional perspective plan view from in front.

The ski goggles 100 shown in FIG. 1 to FIG. 6 have a frame 101, a frame pad 102, a goggle lens 103 in the form of a transparent plastic panel in the visible spectral range, and two sidepieces (104a, 104b) for a retaining strap 120 shown in FIG. 1A.

The goggle lens 103 is supported by the frame 101. For this purpose, the frame 101 has at least in some parts a groove (105a, 105b) into which the goggle lens 103 is inserted at corresponding portions (106a, 106b) of the outer circumference 106. The frame 101 is formed as a single piece and of one material and, in the present illustrative embodiment, is made of polyurethane. The frame 101 is configured in the form of an elongate surround. The frame 101 has a frame rear side 101e directed toward the wearer's face during normal use, a frame front 101f lying opposite the frame rear side 101e, and a frame edge 101g directed laterally outward with a gently convexly curved upper part 101b, referred to hereinbelow as the upper frame-edge portion or upper outer side section, and a lower part 101c, which forms an inwardly curving nose-piece 101d. The frame edge 101q is also referred to as the laterally outwardly orientated frame outer side.

The goggle lens 103 supported by the frame 101 has a surface 103a directed toward the wearer's face during normal use, and a surface 103b directed away from the wearer's face during normal use. In the present illustrative embodiment, the goggle lens 103 is made of polycarbonate. Instead of polycarbonate, the goggle lens 103 can also be made of polyamide.

Figure 4:
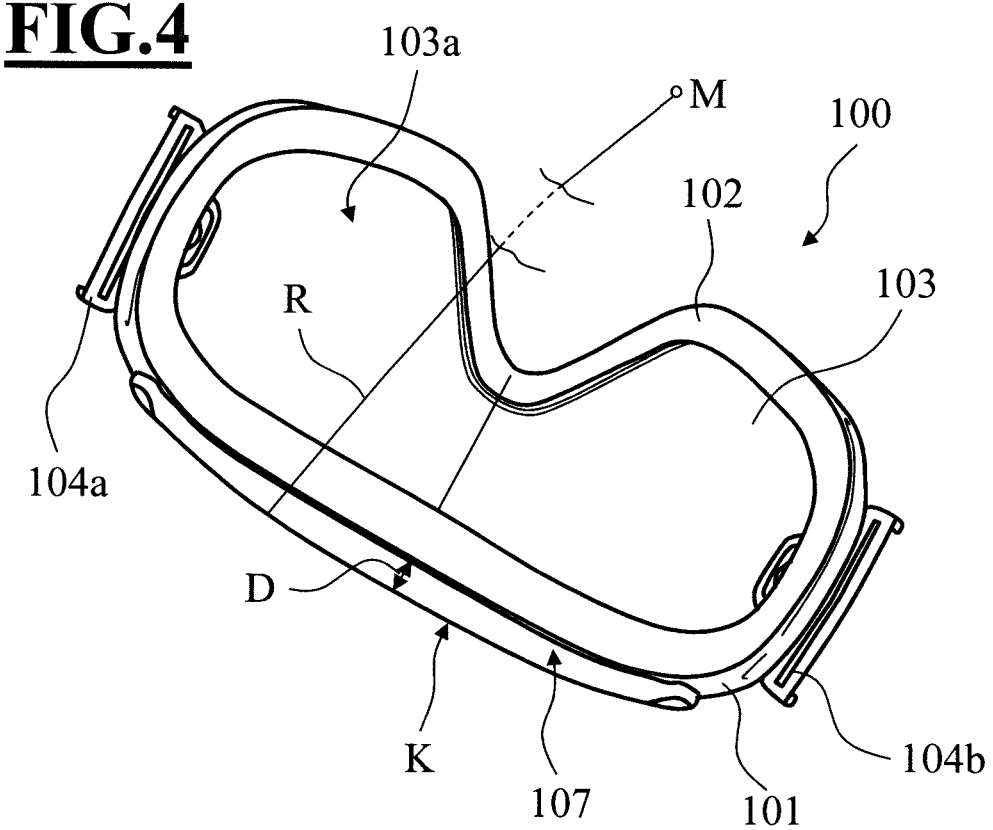
FIG. 4 shows the reverse of the ski goggles according to FIG. 1 in a plan view.

The frame pad 102 is adhesively bonded to that side of the frame 101 directed toward the wearer's face. The frame pad 102 is brought to rest on the wearer's face during normal use. The frame pad 102 is made of a soft foam. The foam can be of an open-pore type, which is preferred in respect of the permeability and capability of storing moisture. The frame pad 102 extends around the entire periphery of the back side of the frame as shown in FIG. 4 and is directed toward the face has a density lower than that of the frame 101.

Frame 101 and frame pad 102 have a concave curvature that respects the shape of the head.

The sidepieces (104a, 104b) are provided for the retaining strap 120 shown in FIG. 1A in phantom outline. The retaining strap 120 holds the ski goggles 100 on the wearer's head during normal use, and are fastened to the rearwardly pointing part 101a of the frame 101. The retaining strap 120 can be composed of a textile fabric. The retaining strap is generally adjustable in length.

Figure 7:
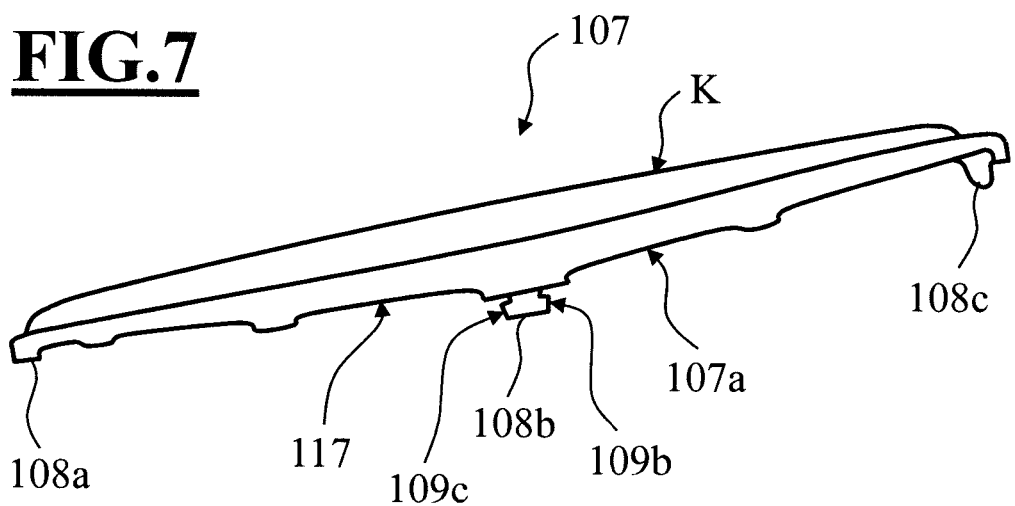
FIG. 7 shows the spoiler of the ski goggles according to FIG. 1 in a plan view from in front; and, FIG. 8 shows a detail of the upper part of the ski goggles with spoiler according to FIG. 1.
Figure 6:
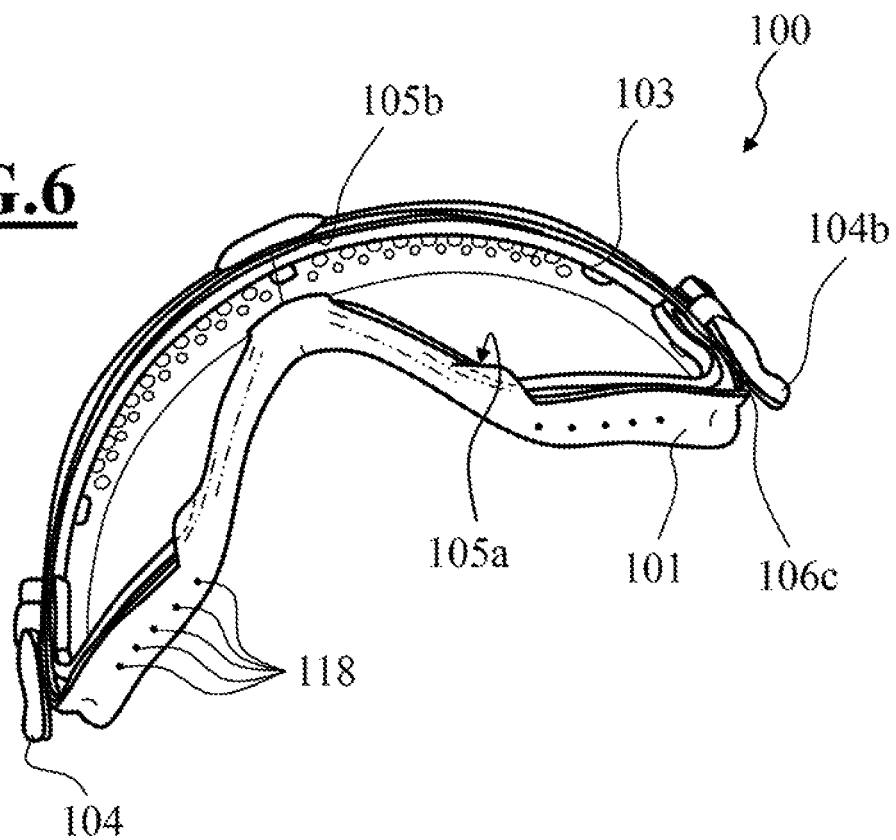
FIG. 6 shows the ski goggles according to FIG. 1 in a plan view of the underside obliquely from in front.

According to the invention, the ski goggles 100 have a spoiler 107, which can be connected releasably to the upper frame-edge portion 101b and is shown separately in FIG. 7.

Figure 2:
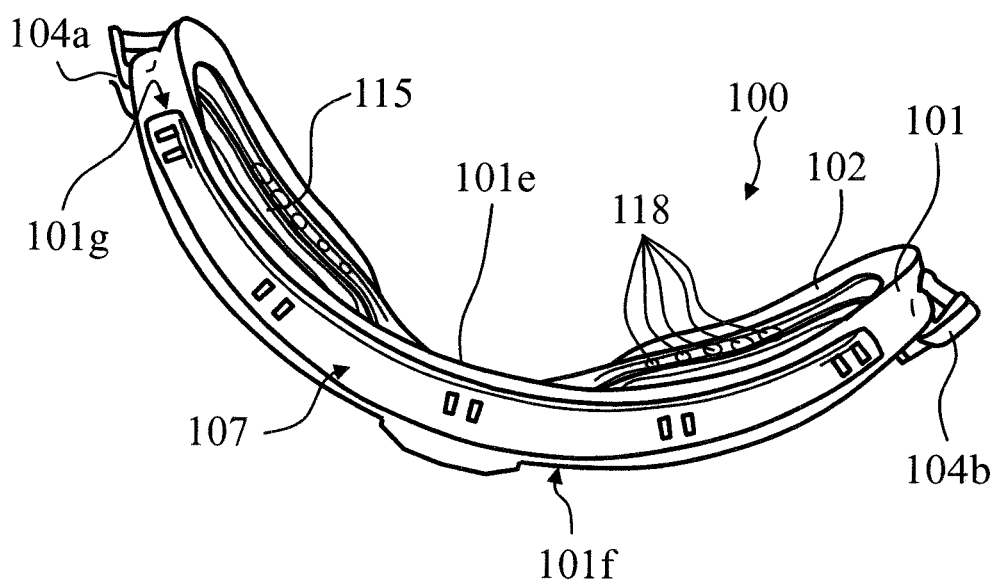
FIG. 2 shows the ski goggles according to FIG. 1 in a plan view from above.

As shown in FIG. 2, the upper frame-edge portion 101b of the goggles frame is curved and defines a predetermined curvature when viewed in plan. The spoiler 107 is curved to correspond to the predetermined curvature of the upper frame-edge portion 101b.

As shown in FIGS. 1 and 2, the spoiler 107 is mounted on the upper frame-edge portion 101b of the goggles frame and extends laterally from approximately the frame front 101f to the frame rear side 101e.

The spoiler 107 according to the invention comprises a fastening mechanism for releasable connection to the upper frame-edge portion 101b of the ski goggles 100. In the illustrative embodiment shown, the fastening mechanism comprises three latches (108a, 108b, 108c), which are arranged on an underside 107a of the spoiler 107 and protrude down from the latter substantially perpendicularly. The latches (108a, 108b, 108c) have horizontally extending lugs (109a, 109b) of which, however, only the ones belonging to the central latch 108b can be seen in FIG. 7.

The latches (108a, 108b, 108c) can engage and lock releasably in corresponding latch openings (110a, 110b, 110c) with corresponding movable lugs (109a, 109b) shown in FIG. 7 in the upper frame-edge portion 101b. In addition, guide webs or guide pins can be provided on the underside of the spoiler and can be introduced into corresponding guide openings in the upper frame-edge portion in order to align spoiler and frame relative to each other preferably with a form fit, but they do not themselves have a latching or locking function and, for example, have no lugs of the type described above. The latch openings (110a, 110b, 110c) are shown from below in FIG. 5.

The lugs of the central latch opening 110b can be forced apart with the aid of a slide 110d, as a result of which the lugs (109a, 109b) of the latch 108b are released and the spoiler 107 can be upwardly removed. The same-shape lugs of the outer latches (108a, 108c) and openings (110a, 110c) are forced apart solely by the force applied when removing the spoiler 107.

Figure 3:
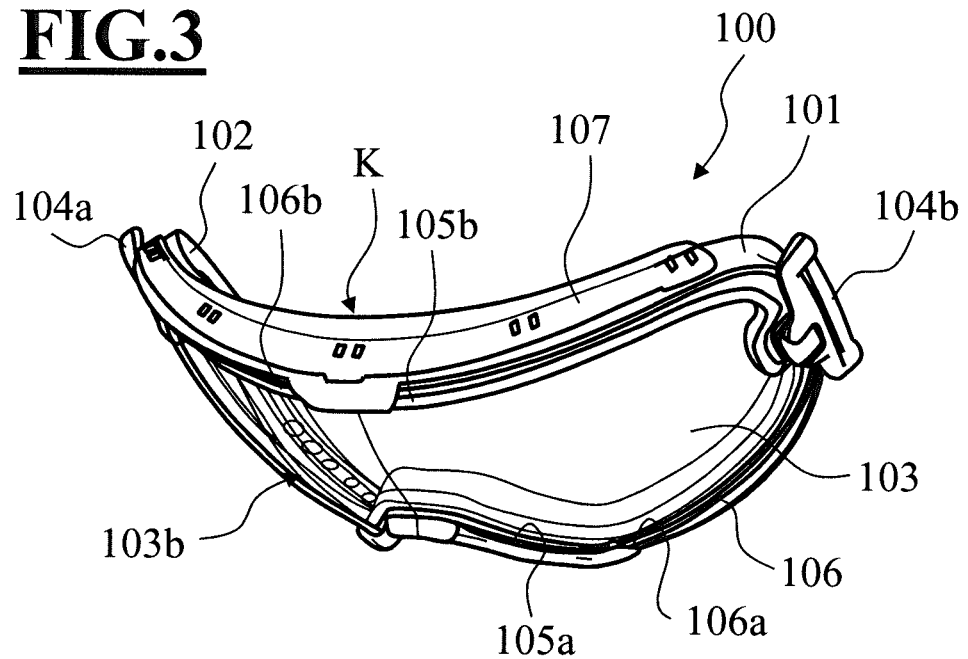
FIG. 3 shows the ski goggles according to FIG. 1 in a plan view obliquely from above.

In its position when locked onto the frame, the spoiler 107 protrudes above the frame 101, as can be seen in particular from FIGS. 1, 3 and 4. In the present illustrative embodiment, the spoiler 107 protrudes above the frame 101 in a central area 111 by a distance D of about 1.5 cm.

The spoiler 107 is designed curving laterally upward in an arc shape. The curvature is indicated in the FIGS. by the reference sign K. The radius of curvature R of the arc K, which is shown in FIG. 4 together with the center of curvature M, measures 75 cm in the present illustrative embodiment.

The spoiler 107 has a spoiler portion 112 directed laterally upward (see directional arrow O in FIG. 1 and FIG. 8) away from the upper frame-edge portion 101b. This spoiler portion 112 is designed in such a way that, during normal use of the ski goggles 100, air that impacts the spoiler 107 from the front is deflected upward and/or sideways with respect to the wearer's face, as is indicated in FIG. 8 with the aid of the directional arrows (113a, 113b).

Figure 8:
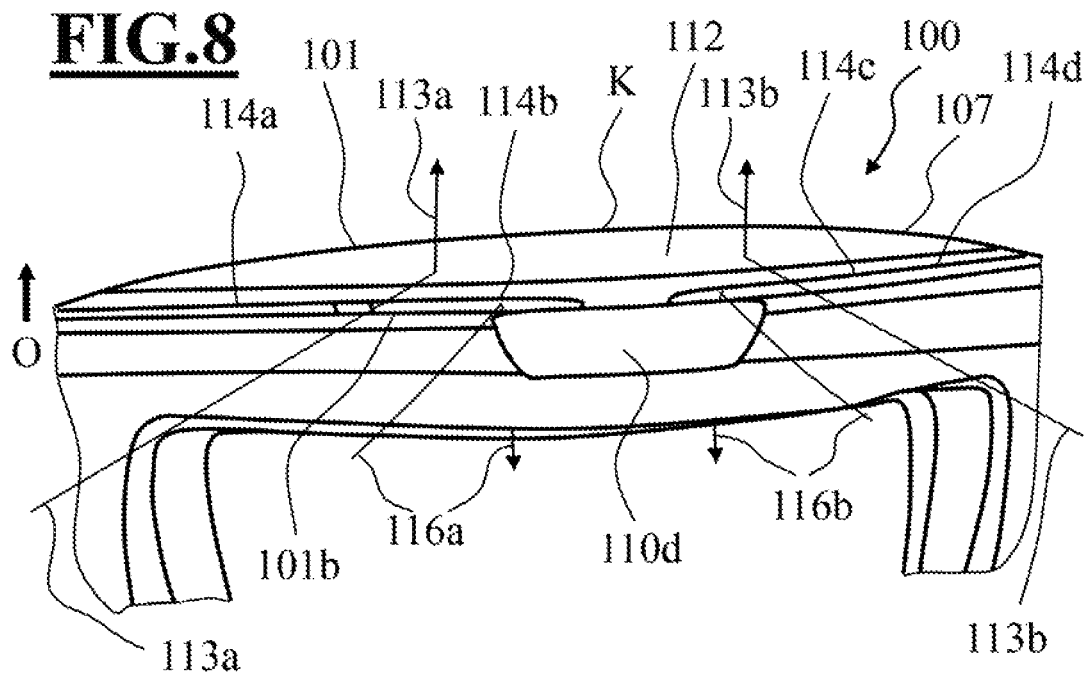

As FIG. 8 shows, the spoiler 107 is solid with no apertures formed therein and increases in elevation from the front upper frame-edge portion 101b. The air streams (113a, 113b) impinge upon the spoiler approximately at the mid region and are deflected vertically upwardly at right angles which show that the spoiler at this mid region has an upward slant of 45°. FIG. 8 further shows that the spoiler continues to rise in elevation and ends at its upper curvature K. Also, as shown in FIG. 2, the spoiler 107 extends laterally from the frame front 101f to the frame rear side 101e.

In the present case, the spoiler 107 has four air inlet recesses (114a, 114b, 114c, 114d) which, during normal use of the ski goggles 100, ensure that air impacting the spoiler 107 from the front is deflected into the space 115 formed, during normal use of the ski goggles 100, between the goggle lens 103 and the wearer's face. This air flow is indicated in FIG. 8 with the aid of the directional arrows bearing the reference signs 116a and 116b. The downwardly pointing spoiler portion is indicated in the drawing by the reference sign 119.

All four air inlet recesses (114a, 114b, 114c, 114d) are designed as openings between spoiler 107 and frame 101. In other words, the openings are formed only by the fact that spoiler 107 and frame 101 are brought to rest on each other but do not bear with a contact fit on each other over the entire contact surface.

As shown in FIG. 8, the spoiler has a lower edge resting on the upper outer side section of the frame when mounted on the ski goggles. The recesses (114a, 114b, 114c, 114d) are formed in the lower edge of the spoiler to define an opening conjointly with the frame to conduct a portion of the impacting air into a space formed between the goggle lens and the face of the wearer. The recess defines the upper periphery of the opening and the upper outer side section of the frame defining the lower periphery of the opening when the spoiler is mounted on the ski goggles.

During normal use of the ski goggles, that is, when the wearer is wearing the ski goggles and the helmet and when the wearer's head is upright, the spoiler 107 protrudes preferably above the frame 101 and in this way fills the gap G shown in FIG. 1 between the top edge 101b of the ski goggles and the bottom edge of the face opening of the helmet indicated by the broken line 130 also shown in FIG. 1. This prevents cold air from flowing onto the otherwise exposed part of the skier's forehead, particularly during skiing.

The spoiler 107 according to the invention has an opening 117 for electronic parts. This is located on the underside 107a of the spoiler 107.

Figure 5:
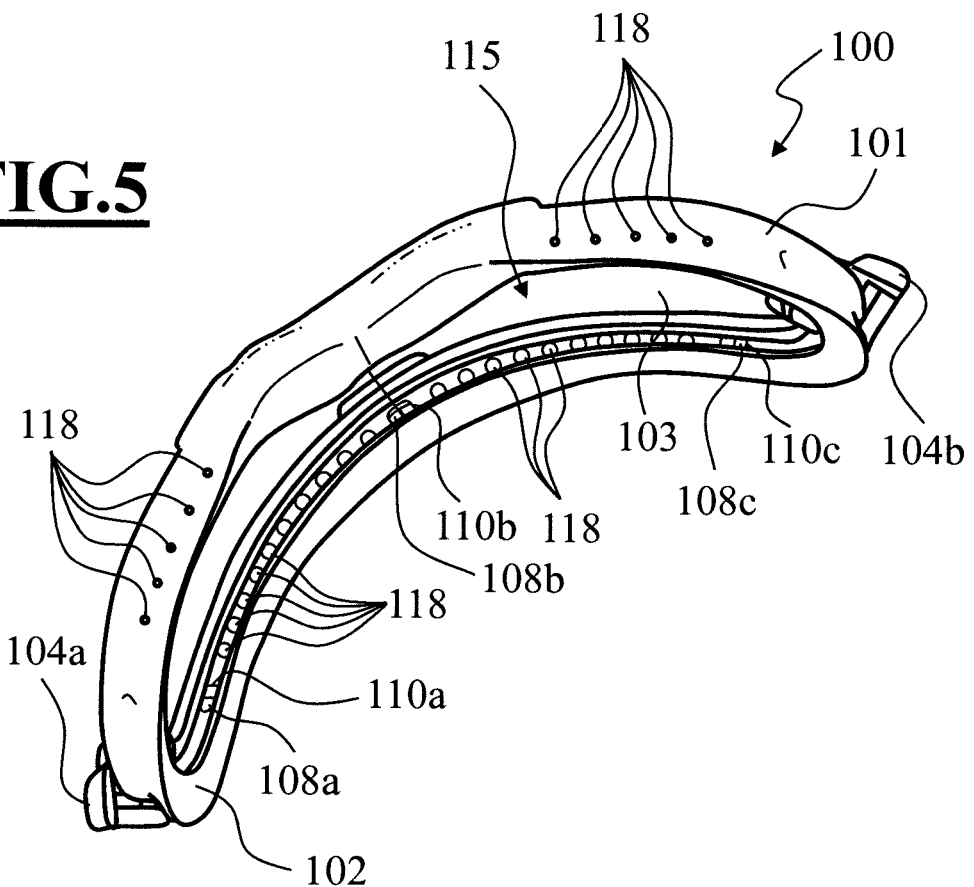
FIG. 5 shows the ski goggles according to FIG. 1 in a plan view from below.

As shown in bottom plan view in FIG. 5, the frame 101 has ventilation openings 118 which, in the direction perpendicular to the surface 103a directed toward the wearer's face during normal use, are arranged between the goggle lens 103 and the frame pad 102. In the illustrative embodiment shown, these ventilation openings 118 are designed as conical bores. Bores 118 are formed in the upper part 101b of the frame 101 in the vertical direction. Bores 118 are also located in the lower part 101c of the frame 101.

It is understood that the foregoing description is that of the preferred embodiments of the invention and that various changes and modifications may be made thereto without departing from the spirit and scope of the invention as defined in the appended claims.

What is claimed is:

1. Ski goggles to be worn on a head and face of a wearer, the ski goggles comprising:

a frame having a frame back side adapted to face toward the wearer and defining a periphery and a frame pad made of soft foam bonded to said frame back side so as to extend around the entire periphery thereof;

a goggle lens held in said frame;

said frame back side being adapted to be brought to rest with said frame pad on the face of the wearer during normal use to define an enclosed space between said goggle lens and the face of the wearer;

said frame further having a frame front side lying opposite said frame back side and a laterally outwardly oriented frame outer side including an upper outer side section extending from said frame front side to said frame back side and being curved to define a predetermined curvature when viewed in plan;

a retaining strap adapted to hold the ski goggles on and against the head of the wearer during normal use;

a spoiler disposed on said upper outer side section of said frame;

said frame and said spoiler conjointly defining an interface;

a fastening mechanism arranged at said interface for releasably connecting said spoiler to said frame;

said spoiler being without an aperture formed therein and being curved to correspond to said predetermined curvature of said upper outer side section when viewed in plan;

said spoiler having a lower edge at said interface and said spoiler extending from said front side of said frame whereat said lower edge of said spoiler is in contact with said upper outer side section at said frame front side and said spoiler increasing upwardly in elevation and away from said upper outer side section of said frame and tapering upwardly from each lateral end of said frame to a location halfway between said lateral ends with said spoiler forming an arc (K) having a radius of curvature (R) causing said spoiler to protrude above said frame and be in spaced relationship to said upper outer side section and with the increasing elevation of said spoiler and said predetermined curvature thereof adapted to cause air impacting on said spoiler to be deflected upward away from the face of the wearer and sideways away from the face of the wearer;

said spoiler having at least one recess formed in said lower edge thereof to define an opening at said interface conjointly with said frame to conduct a portion of the impacting air into said space; and, said at least one recess defining the upper periphery of said opening and said upper outer side section of said frame defining the lower periphery of said opening.

2. The ski goggles of claim 1, wherein:

the ski goggles define an upward direction; and, said spoiler projects beyond said frame in said upward direction.

3. The ski goggles of claim 2, wherein:
said frame defines a central region; and,
said spoiler projects beyond said upper outer side section of said frame in said upward direction in said central region by 0.4 centimeters to 2 centimeters.

4. The ski goggles of claim 2, wherein:
said frame defines a central region; and,
said spoiler projects beyond said frame in said upward direction in said central region by 0.4 centimeters to 1.5 centimeters.

5. The ski goggles of claim 2, wherein:
said frame defines a central region; and,
said spoiler projects beyond said upper outer side section of said frame in said upward direction in said central region by 0.4 centimeters to 1 centimeter.

6. The ski goggles of claim 1, wherein:
the ski goggles define an upward direction; and,
said spoiler is curved laterally in said upward direction in an arc-shape.

7. The ski goggles of claim 6, wherein said spoiler is curved laterally in said upward direction in an arc shape with a curvature radius (R) lying in a range of 10 centimeters to 100 centimeters.

8. The ski goggles of claim 6, wherein said spoiler is curved laterally in said upward direction in an arc shape with a curvature radius (R) lying in a range of 15 centimeters to 90 centimeters.

9. The ski goggles of claim 6, wherein said spoiler is curved laterally in said upward direction in an arc shape with a curvature radius (R) lying in a range of 20 centimeters to 80 centimeters.

10. The ski goggles of claim 6, wherein said spoiler is curved laterally in said upward direction in an arc shape with a curvature radius (R) lying in a range of 30 centimeters to 70 centimeters.

11. Ski goggles adapted to be worn on a head and face of a wearer wearing a helmet, the ski goggles comprising:
a frame having a frame back side defining a periphery and a frame pad made of soft foam bonded to said frame back side so as to extend around the entire periphery thereof;
a goggle lens held in said frame;
said frame back side being adapted to be brought to rest with said frame pad on the face of the wearer during normal use to define an enclosed space between said goggle lens and the face of the wearer;
said frame further having a frame front side lying opposite said frame back side and a laterally outwardly oriented frame outer side including an upper outer side section extending from said frame front side to said frame back side and being curved to define a predetermined curvature when viewed in plan;
a retaining strap adapted to hold the ski goggles on and against the head of the wearer during normal use;
a spoiler disposed on said upper outer side section of said frame;
said frame and said spoiler conjointly defining an interface;
a fastening mechanism arranged at said interface for releasably connecting said spoiler to said frame;
a gap being formed between the helmet and said upper outer side section of said frame when the ski goggles are worn by the wearer and wherein the ski goggles define an upward direction and a frontal direction;

said spoiler being without apertures formed therein and being directed away from said upper outer side section laterally in the upward direction to reduce or close said gap to protect the wearer from cold air;
said spoiler being curved to correspond to said predetermined curvature of said upper outer side section when viewed in plan; and,
said spoiler having a lower edge at said interface and said spoiler extending from said front side of said frame whereat said lower edge of said spoiler is in contact with said frame and increasing upwardly in elevation and away from said upper outer side section of said frame and tapering upwardly from said each lateral end of said frame to a location halfway between said lateral ends with said spoiler forming an arc (K) having a radius of curvature (R) causing said spoiler to protrude above said frame at a predetermined distance D therefrom and be in spaced relationship to said frame and with the increasing elevation of said spoiler and said predetermined curvature thereof adapted to cause air impacting on said spoiler to be deflected upward away from the face of the wearer and sideways away from the face of the wearer;
said spoiler having at least one recess formed in said lower edge thereof to define an opening at said interface conjointly with said frame to conduct a portion of the impacting air into said space; and,
said at least one recess defining the upper periphery of said opening and said upper outer side section of said frame defining the lower periphery of said opening.

12. The ski goggles of claim 11, wherein:
said spoiler has a spoiler section facing toward said upper outer side section and laterally downwardly; and,
said spoiler section includes at least one air inlet.

13. The ski goggles of claim 11, wherein said spoiler includes a seat for electronic parts.

14. The ski goggles of claim 11, wherein said spoiler is at least partially made of a flexible plastic having a modulus of elasticity between 2 Newton/(millimeter)$^2$ and 100 Newton/(millimeter)$^2$.

15. The ski goggles of claim 11, wherein said spoiler is made at least in part from a same material as the frame.

16. A spoiler for ski goggles adapted to be worn on a head and face of a wearer and the ski goggles having a goggle lens and frame with a frame front side, a frame back side and an upper outer side section extending from said frame front side to said frame back side and being curved to define a predetermined curvature when viewed in plan, the frame back side defining a periphery and having a soft foam bonded thereto so as to extend around all of said periphery, the frame back side being adapted to be brought to rest on the face of the wearer with said soft foam to define an enclosed space between the goggle lens and the face of the wearer, the spoiler comprising:
a spoiler body;
a fastening arrangement configured to releasably connect said spoiler body to the ski goggles at the upper outer side section;
said spoiler being without apertures formed therein and being curved to correspond to said predetermined curvature of said upper outer side section and said spoiler being adapted to extend from said frame front side whereat said spoiler is in contact with said frame and increasing upwardly in elevation and away from said upper outer side section of said frame and tapering upwardly from each lateral end of said frame to a location halfway between said lateral ends with said spoiler forming a continuous uninterrupted arc (K) having a radius of curvature (R) to protrude above said frame and be in spaced relationship to said frame and with the increasing elevation of said spoiler and said predetermined curvature thereof adapted to cause air impacting on said spoiler to be deflected upward away from the face of the wearer and sideways away from the face of the wearer;

said spoiler having a plurality of recesses formed in said lower edge thereof, each recess defining a respective opening conjointly with said frame to conduct a portion of the impacting air into said space; and, each recess defining the upper periphery of said respective opening and said upper outer side section of said frame defining the lower periphery of said respective opening when said spoiler is mounted on said ski goggles.

17. Ski goggles to be worn on a head and face of a wearer, the ski goggles comprising:

a frame having a frame back side adapted to face toward the wearer and defining a periphery and a frame pad made of soft foam bonded to said frame back side so as to extend around the entire periphery thereof;

a goggle lens held in said frame;

said frame back side being adapted to be brought to rest with said frame pad on the face of the wearer during normal use to define an enclosed space between said goggle lens and the face of the wearer;

the frame further having a frame front side lying opposite the frame back side;

a laterally outwardly oriented frame outer side including an upper outer side section extending from said frame front side to said frame back side;

said upper outer side section being curved to define a predetermined curvature when viewed in plan;

a retaining strap adapted to hold the ski goggles on and against the head of the wearer during normal use;

a spoiler body;

said spoiler body and said upper outer side section of said frame conjointly defining an interface;

a fastening arrangement at said interface to releasably connect said spoiler body to the upper outer side section;

said fastening arrangement including a plurality of latches formed on said spoiler body and a plurality of latch openings formed in said frame for receiving corresponding ones of said plurality of latches when said spoiler body is releasably connected to said frame;

said spoiler body being curved to correspond to said predetermined curvature of said upper outer side section when viewed in plan;

said spoiler having a lower edge at said interface and said spoiler extending from said front side of said frame whereat said spoiler is in contact with said upper outer side section at said frame front side and said spoiler increasing upwardly in elevation and away from said upper outer side section of said frame and tapering upwardly from each lateral end of said frame to a location halfway between lateral ends with said spoiler forming an arc (K) having a radius of curvature (R) causing said spoiler to protrude above said frame and be in spaced relationship to said upper outer side section and with the increasing elevation of said spoiler and said predetermined curvature thereof adapted to cause air impacting on said spoiler to be deflected upward away from the face of the wearer and sideways away from the face of the wearer;

said spoiler having at least one recess formed in said lower edge thereof to define an opening at said interface conjointly with said frame to conduct a portion of the impacting air into said space; and, said at least one recess defining the upper periphery of said opening and said upper outer side section of said frame defining the lower periphery of said opening.

18. Ski goggles to be worn on a head and face of a wearer, the ski goggles comprising:

a frame having a frame back side adapted to face toward the wearer and defining a periphery and a frame pad made of soft foam bonded to said frame back side so as to extend around the entire periphery thereof;

a goggle lens held in said frame;

said frame back side being adapted to be brought to rest with said frame pad on the face of the wearer during normal use to define an enclosed space between said goggle lens and the face of the wearer;

said frame further having a frame front side lying opposite said frame back side and a laterally outwardly oriented frame outer side including an upper outer side section extending from said frame front side to said frame back side and being curved to define a predetermined curvature when viewed in plan;

a retaining strap adapted to hold the ski goggles on and against the head of the wearer during normal use;

said frame having mutually opposite lateral ends with said goggle lens being accommodated therebetween;

first and second side pieces formed on corresponding ones of said lateral ends for connecting said retaining strap to said frame;

said retaining strap being composed of a length-adjustable textile or rubber strap;

a spoiler releasably connected to said upper outer side section;

said spoiler and said upper outer side section conjointly defining an interface;

a fastening arrangement disposed at said interface and including one or more latches for engaging corresponding one or more latch openings formed in said upper outer side section to releasably attach said spoiler to said frame;

said spoiler being curved to correspond to said predetermined curvature of said upper outer side section when viewed in plan;

said spoiler having a lower edge at said interface and said spoiler extending from said front side of said frame whereat said spoiler is in contact with said upper outer side section at said frame front side of said frame and said spoiler increasing upwardly in elevation from said upper outer side section and away from said frame and tapering upwardly from each lateral end of said frame to a location halfway between said lateral ends with said spoiler forming an arc (K) having a radius of curvature (R) causing said spoiler to protrude above said frame and be in spaced relationship to said upper outer side section and with the increasing elevation of said spoiler and said predetermined curvature thereof adapted to cause air impacting on said spoiler to be deflected upward away from the face of the wearer and sideways away from the face of the wearer;

said spoiler having at least one recess formed in said lower edge thereof to define an opening at said interface conjointly with said frame to conduct a portion of the impacting air into said space; and, said at least one recess defining the upper periphery of said opening and said upper outer side section of said frame defining the lower periphery of said opening.

19. Ski goggles to be worn on a head and face of a skier wearing a helmet so that a gap is formed between the helmet and the ski goggles, the ski goggles comprising:
a frame having a frame back side adapted to face toward the wearer and defining a periphery and a frame pad made of soft foam bonded to said frame back side so as to extend around the entire periphery thereof;
a goggle lens held in said frame;
said frame back side being adapted to be brought to rest with said frame pad on the face of the skier during normal use to define an enclosed space between said goggle lens and the face of the wearer;
said frame further having a frame front side lying opposite said frame back side and a laterally outwardly oriented frame outer side including an upper outer side section extending from said frame front side to said frame back side and being curved to define a predetermined curvature when viewed in plan;
a retaining strap adapted to hold the ski goggles on and against the head of the skier during normal use;
a spoiler configured to be releasably connected to said upper outer side section;
said spoiler and said frame conjointly defining an interface;
said spoiler being curved to correspond to said predetermined curvature of said upper outer side section when viewed in plan;
said spoiler having a lower edge at said interface and said spoiler extending from said front side of said frame whereat said spoiler is in contact with said upper outer side section at said frame front side of said frame and said spoiler increasing upwardly in elevation away from said upper outer side section and away from said frame and tapering upwardly from each lateral end of said frame to a location halfway between said lateral ends with said spoiler forming an arc (K) having a radius of curvature (R) causing said spoiler to protrude above said frame to bridge said gap and be in spaced relationship to said upper outer side section at said frame back side and with the increasing elevation of said spoiler and said predetermined curvature thereof adapted to cause air impacting on said spoiler to be deflected upward away from the face of the wearer and sideways away from the face of the wearer;
said spoiler having at least one recess formed in said lower edge thereof to define an opening at said interface conjointly with said frame to conduct a portion of the impacting air into said space; and,
said at least one recess defining the upper periphery of said opening and said upper outer side section of said frame defining the lower periphery of said opening.

20. Ski goggles to be worn on a head and face of a wearer, the ski goggles comprising:
a goggle lens;
a frame having a frame back side adapted to face toward the wearer and defining a periphery and a frame pad made of soft foam bonded to said frame back side so as to extend around the entire periphery thereof;
said frame back side being adapted to be brought to rest with said frame pad on the face of the wearer during normal use;
said frame further having a frame front side lying opposite said frame back side and a laterally outwardly oriented frame outer side including an upper outer side section extending from said frame front side to said frame back side and being curved to define a predetermined curvature when viewed in plan;
said goggle lens being held in said frame;
a retaining strap adapted to hold the ski goggles on and against the head of the wearer during normal use;
a spoiler configured to be releasably connected to said upper outer side section of said frame;
said spoiler and said frame conjointly defining an interface;
said spoiler being without apertures formed therein and being curved to correspond to said predetermined curvature of said upper outer side section when viewed in plan;
said spoiler having a lower edge at said interface and said spoiler extending from said front side of said frame whereat said spoiler is in contact with said upper outer side section at said frame front side of said frame and said spoiler increasing upwardly in elevation from said upper outer side section and away from said frame and tapering upwardly from each lateral end of said frame to a location halfway between said lateral ends with said spoiler forming an arc (K) having a radius of curvature (R) adapted to cause said spoiler to protrude above said frame and be in spaced relationship to said upper outer side section at said frame back side and with the increasing elevation of said spoiler causing air impacting on said spoiler to be deflected upward away from the face of the wearer and sideways away from the face of the wearer;
said goggle lens, said frame and said frame pad being conjointly adapted to define an intermediate closed off space with the face of the wearer during normal use of the ski goggles;
said spoiler having a plurality of recesses formed in said lower edge thereof, each recess defining a respective opening with said frame at said front side of said frame to guide air impacting said spoiler during normal use of the ski goggles into said intermediate closed off space to provide ventilation to prevent misting in said intermediate closed off space; and,
each recess defining the upper periphery of said respective opening and said upper outer side section of said frame defining the lower periphery of said respective opening.

21. Ski goggles to be worn on a head and face of a wearer, the ski goggles comprising:
a frame having a frame back side adapted to face toward the wearer and defining a periphery and a frame pad made of soft foam bonded to said frame back side so as to extend around the entire periphery thereof;
a goggle lens held in said frame;
said frame back side being adapted to be brought to rest with said frame pad on the face of the wearer during normal use to define an enclosed space between said goggle lens and the face of the wearer;
said frame further having a frame front side lying opposite said frame back side and a laterally outwardly oriented frame outer side including an upper outer side section extending from said frame front side to said frame back side and being curved to define a predetermined curvature when viewed in plan;
a retaining strap adapted to hold the ski goggles on and against the head of the wearer during normal use;
a spoiler disposed on said upper outer side section of said frame;
said frame and said spoiler conjointly defining an interface;

a fastening mechanism arranged at said interface for releasably connecting said spoiler to said frame;

said spoiler being curved to correspond to said predetermined curvature of said upper outer side section when viewed in plan;

said spoiler having a lower edge at said interface and said spoiler extending from said front side of said frame whereat said lower edge of said spoiler is in contact with said upper outer side section at said frame front side and said spoiler increasing upwardly in elevation and away from said upper outer side section of said frame and tapering upwardly from each lateral end of said frame to a location halfway between said lateral ends with said spoiler forming an arc (K) having a radius of curvature (R) causing said spoiler to protrude above said frame and be in spaced relationship to said upper outer side section and with the increasing elevation of said spoiler and said predetermined curvature thereof adapted to cause air impacting on said spoiler to be deflected upward away from the face of the wearer and sideways away from the face of the wearer;

at least one ventilating opening formed in said frame extending from said upper outer side section into said enclosed space between said goggle lens and the face of the wearer;

said spoiler having a plurality of recesses formed in said lower edge thereof, each recess defining a respective air inlet recess at said interface conjointly with said upper outer side section of said frame to conduct a portion of the impacting air into said enclosed space to prevent misting of the ski goggles during normal use thereof; and, each recess defining the upper periphery of said respective air inlet recess and said upper outer side section of said frame defining the lower periphery of said respective air inlet recess.

* * * * *

UNITED STATES PATENT AND TRADEMARK OFFICE
CERTIFICATE OF CORRECTION

PATENT NO. : 10,857,035 B2
APPLICATION NO. : 14/673296
DATED : December 8, 2020
INVENTOR(S) : Roberto Padovani It is certified that error appears in the above-identified patent and that said Letters Patent is hereby corrected as shown below:

In the Claims

<u>In Column 8:</u>
Delete Lines 59 to 65 Claim 1: and insert -- said spoiler having a plurality of recesses formed in said lower edge thereof, each recess defining a respective opening at said interface conjointly with said frame to conduct a portion of the impacting air into said space; and,
  each recess defining the upper periphery of said respective opening and said upper outer side section of said frame defining the lower periphery of said respective opening. -- therefor.

<u>In Column 10:</u>
Delete Lines 24 to 30 Claim 11: and insert -- said spoiler having a plurality of recesses formed in said lower edge thereof, each recess defining a respective opening at said interface conjointly with said frame to conduct a portion of the impacting air into said space; and,
  each recess defining the upper periphery of said respective opening and said upper outer side section of said frame defining the lower periphery of said respective opening. -- therefor.

<u>In Column 11:</u>
Delete Lines 9 to 17 Claim 16: and insert -- said spoiler having a lower edge resting on said upper outer side section of said frame when mounted on said ski goggles;
  said spoiler having a plurality of recesses formed in said lower edge thereof, each recess defining a respective opening conjointly with said frame to conduct a portion of the impacting air into said space; and, Signed and Sealed this
Twenty-fourth Day of August, 2021

Drew Hirshfeld
*Performing the Functions and Duties of the
Under Secretary of Commerce for Intellectual Property and
Director of the United States Patent and Trademark Office* each recess defining the upper periphery of said respective opening and said upper outer side section of said frame defining the lower periphery of said respective opening when said spoiler is mounted on said ski goggles. -- therefor.

In Column 12:
Delete Lines 1 to 7 Claim 17: and insert -- said spoiler having a plurality of recesses formed in said lower edge thereof, each recess defining a respective opening at said interface conjointly with said frame to conduct a portion of the impacting air into said space; and, each recess defining the upper periphery of said respective opening and said upper outer side section of said frame defining the lower periphery of said respective opening. -- therefor.

In Column 12 and 13:
Delete Column 12, Lines 64 to 67 and Column 13, Lines 1 to 3 Claim 18: and insert -- said spoiler having a plurality of recesses formed in said lower edge thereof, each recess defining a respective opening at said interface conjointly with said frame to conduct a portion of the impacting air into said space; and, each recess defining the upper periphery of said respective opening and said upper outer side section of said frame defining the lower periphery of said respective opening. -- therefor.

In Column 13:
Delete Lines 48 to 54 Claim 19: and insert -- said spoiler having a plurality of recesses formed in said lower edge thereof, each recess defining a respective opening at said interface conjointly with said frame to conduct a portion of the impacting air into said space; and, each recess defining the upper periphery of said respective opening and said upper outer side section of said frame defining the lower periphery of said respective opening. -- therefor.